(12) United States Patent
Matsuzaki et al.

(10) Patent No.: US 9,795,806 B2
(45) Date of Patent: Oct. 24, 2017

(54) PARTICLE BEAM THERAPY SYSTEM, AND METHOD FOR OPERATING PARTICLE BEAM THERAPY SYSTEM

(71) Applicant: HITACHI, LTD., Tokyo (JP)

(72) Inventors: Kazuki Matsuzaki, Tokyo (JP); Toru Umekawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/029,385

(22) PCT Filed: Oct. 22, 2014

(86) PCT No.: PCT/JP2014/078035
§ 371 (c)(1),
(2) Date: Apr. 14, 2016

(87) PCT Pub. No.: WO2015/060330
PCT Pub. Date: Apr. 30, 2015

(65) Prior Publication Data
US 2016/0263399 A1   Sep. 15, 2016

(30) Foreign Application Priority Data

Oct. 25, 2013   (JP) .................................. 2013-222299

(51) Int. Cl.
*A61N 5/10*   (2006.01)
(52) U.S. Cl.
CPC ........... *A61N 5/107* (2013.01); *A61N 5/1039* (2013.01); *A61N 5/1049* (2013.01);
(Continued)
(58) Field of Classification Search
CPC .... A61N 5/1039; A61N 5/1049; A61N 5/107; A61N 2005/1061; A61N 2005/1063; A61N 2005/1087
See application file for complete search history.

(56) References Cited

U.S. PATENT DOCUMENTS

2012/0207372 A1   8/2012   Ichihashi et al.

FOREIGN PATENT DOCUMENTS

| JP | 2011-200542 A | 10/2011 |
|---|---|---|
| JP | 2013-099431 A | 5/2013 |
| WO | 2012/008542 A1 | 1/2012 |

OTHER PUBLICATIONS

Masahide et al, Machine translation (WO 2012/008542 A1), accessed Mar. 10, 2017.*

(Continued)

*Primary Examiner* — Edward Park
(74) *Attorney, Agent, or Firm* — Mattingly & Malur, PC

(57) ABSTRACT

Visualizing a deformation amount or displacement amount of a region of interest in therapy rendered in an image upon aligning images used in radiation therapy allows for enhancing an accuracy of alignment. In a positioning system 104, an image processing unit 201 calculates a deformation parameter using a non-rigid registration method for a region of interest having been set by a treatment planning device 101 based on a treatment plan CT image and three-dimensional tomographic image imaged for bed positioning and calculates a displacement amount parameter for a region extracted using a region extraction method. The image processing unit 201 calculates a positioning parameter representing a displacement amount of a bed based on the calculated deformation parameter and displacement amount parameter and displays the respective parameters together with an alignment image, thereby allowing for confirmation of the deformation amount and displacement amount.

16 Claims, 10 Drawing Sheets

(52) U.S. Cl.
CPC ................. *A61N 2005/1061* (2013.01); *A61N 2005/1063* (2013.01); *A61N 2005/1087* (2013.01)

(56) References Cited

OTHER PUBLICATIONS

Shinichiro et al, Machine translation (JP 2013099431 A), accessed Mar. 10, 2017.*
International Search Report of PCT/JP2014/078035 dated Jan. 27, 2015.

* cited by examiner

FIG. 9
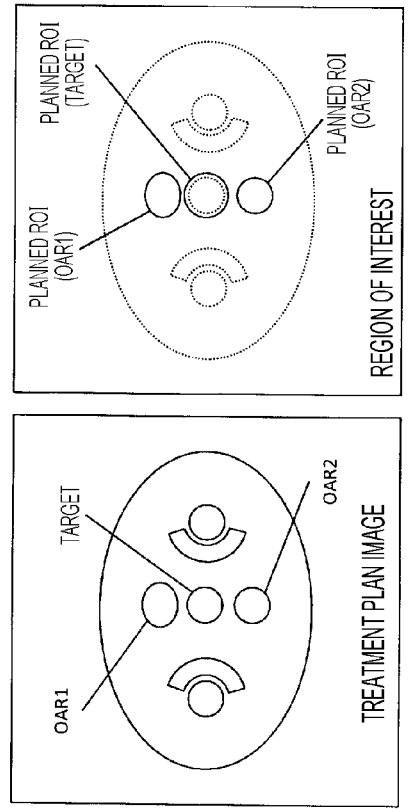
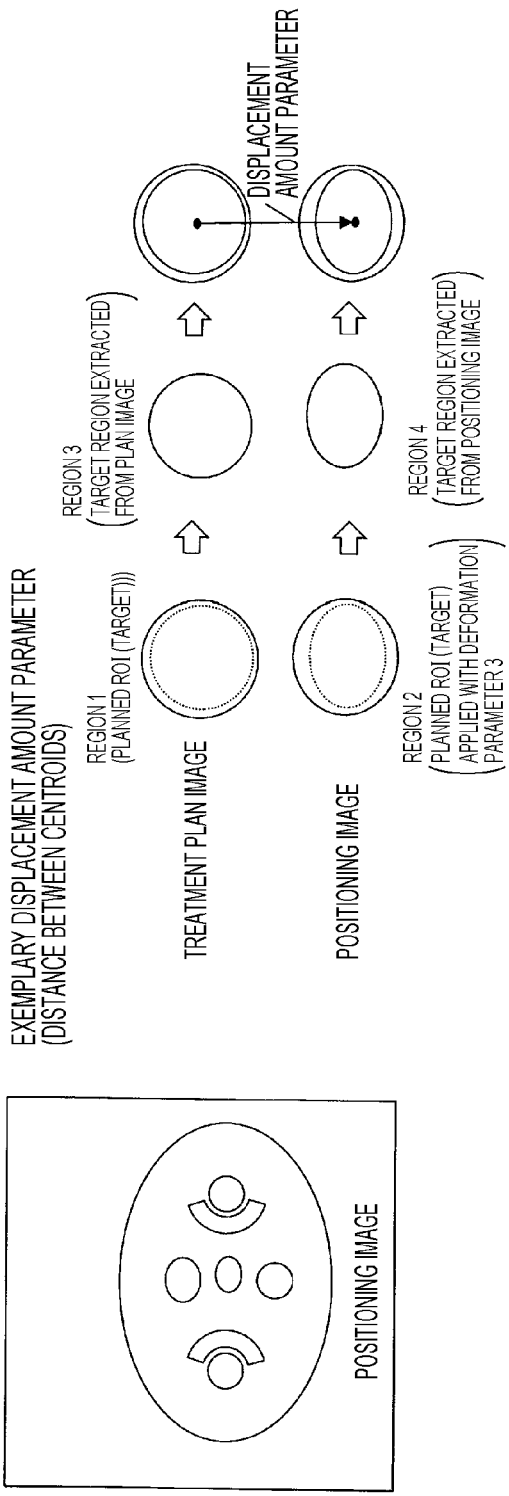

PARTICLE BEAM THERAPY SYSTEM, AND METHOD FOR OPERATING PARTICLE BEAM THERAPY SYSTEM

TECHNICAL FIELD

The present invention relates to radiation therapy apparatuses, systems, and positioning methods and particularly to a radiation therapy apparatus, system, and positioning method for aligning an object rendered in images in radiation therapy where treatment is carried out by irradiating an affected part with various radioactive rays such as particle beams including an X ray and proton beam.

BACKGROUND ART

Recently, radiation therapy to cause tumor cell necrosis by irradiation with various radioactive rays has been widely performed. The radioactive rays used in the art include not only an X ray that is most widely used but also particle beams including a proton beam. Therapy using an X ray or particle beams is also performed. Radiation therapy is usually performed by four steps of diagnosis, treatment plan, treatment, and follow-up examinations. In each of the steps, image guided radiation therapy (IGRT) is increasingly performed using images or image processing technique aiming at more accurate treatment. In the step of diagnosis, for example, with more variations and higher performance of diagnostic devices, structural images of magnetic resonance (MR) images or functional images of positron emission tomography (PET) images are used for determination of treatment regions in treatment plans in addition to X ray computed tomography (CT) images that has been conventionally used for treatment plans.

Meanwhile, one of important processes in a treatment is positioning of a bed. This is to match the current bed position to a position in the treatment plan upon setting up a patient immediately before the treatment. In radiation therapy in general, an affected part is irradiated with radioactive rays multiple times (depends on a treatment part, for example several tens of times) and thus bed positioning is performed each time upon irradiation. Specifically, it is a process of calculating or determining a shift between a position of irradiation target determined in the treatment plan and a current position of the irradiation target on a therapeutic bed (hereinafter abbreviated as "bed") by comparison, by an engineer or doctor, between a digital reconstructed radiograph (DRR) image output from a treatment planning device and an X ray image (digital radiograph (DR) image) photographed using an X ray imaging device while a patient is lying on the bed before irradiation of radioactive rays, thereby obtaining a displacement amount of the bed such that the images of the two types match with each other, and thereby moving the bed.

In this manner, for treatment plans of radiation therapy, treatment, or bed positioning, methods for aligning corresponding positions of a plurality of images include a registration technique. Conventionally, rigid registration has been the mainstream where a displacement amount is obtained with an assumption that an imaging object in an image is not deformed. In radiation therapy, however, an imaging object is human and subjected to non-rigid deformation. Therefore, non-rigid registration corresponding to such deformation started to be in use in CT images for treatment plans. One of such a technique, PTL 1 proposes a method for deforming a region of interest set in a treatment plan and recognizing a target.

CITATION LIST

Patent Literature

PTL 1: JP 2011-200542 A

SUMMARY OF INVENTION

Technical Problem

As described above, bed positioning methods in radiation therapy are widespread. Of these, bed positioning using DR images and DRR images (hereinafter referred to as DRDRR bed positioning) is capable of accurately detecting three degrees of freedom in parallel movement and two degrees of freedom in rotation (rotation on a plane) around an axis of photographing direction. However, it is known that automatically detecting rotation (rotation outside a plane) around an axis perpendicular to an X ray photographing direction is usually difficult. Thus, it is assumed difficult to implement bed positioning with a high accuracy by this method.

As a positioning method capable of automatically detecting six degrees of freedom with the same device as that of the conventional DR-DRR bed positioning, a method using CT images and DR images in a bed positioning system (hereinafter referred to as CT-DR bed positioning) is known. In the DR-DRR bed positioning, a displacement amount is calculated by comparing pixel values of a DRR image generated only for a treatment plan position and a DR image imaged by an X ray imaging device. Contrary to this, in CT-DR bed positioning, DRR images are produced from various angles from a treatment plan CT image and a displacement amount is calculated by comparing pixel values with a DR image. The DRR images can be produced from all directions from the treatment plan CT image and thus six degrees of freedom can be detected. Here, X ray images (DR images) and DRR images are so-called projection images and thus structures with a high absorption ratio of X rays such as bones are mainly projected. Therefore, when a tumor region exists in soft tissues such as organs, observing a tumor position directly from an image may be difficult and an outline or region of an organ itself may also be unclear. Reasons for this include that an X ray image includes data of a three-dimensional structure of a human body projected on a two dimensional plane, and that when a plurality of soft tissues overlap in a projection direction discriminating boundaries thereof may be difficult since an X ray absorption coefficient of soft tissues is lower as compared to that of bones and differences between coefficient values of respective organs are small. Therefore, conventionally, for bed positioning using an X ray image, positioning has been performed assuming that locational relationship between a tumor region (soft tissue) and a bone does not drastically change. In reality however, locations of organs in the body slightly change every day. Therefore, a position of an organ in a CT image in a treatment plan does not necessarily match a position of the organ on a bed upon treatment.

Since the treatment plan CT image is originally a three-dimensional image, a three-dimensional image of a patient is acquired immediately before treatment by a cone beam CT device for imaging while the device is revolving around the patient using an X ray tube and flat panel detector attached to a gantry of a radiation therapy system. Recently, bed positioning using this three-dimensional image has started to be in use (hereinafter referred to as CT-CT bed positioning). The cone beam CT image has inferior image quality as compared to that of the treatment plan CT image; however, a three-dimensional tomographic image can be imaged. This can solve the problem of the aforementioned DR-DRR bed positioning that is insufficient accuracy with degrees of freedom or the problem with a projection image for CT-DR bed positioning. Furthermore, instead of a cone beam CT device attached to a radiation therapy system, in-room CT imaging has been in used where a CT device is installed in a treatment room and a patient is imaged on a common bed, allowing for performing bed positioning with the same image quality as that of the treatment plan CT image.

In this manner, the mainstream in bed positioning is transiting from conventional DR-DRR bed positioning and CT-DRR bed positioning using two dimensional projection images to CT-CT bed positioning using three-dimensional images. This is because an information quantity included in an image has increased due to transition from alignment of two dimensional projection images to three-dimensional tomographic images and thus soft tissues such as a target or organ at risk, which have been relatively difficult to recognize, have become recognizable.

Such recognition has been enabled, however, soft tissues such as a target or organ at risk change every day as described above and thus such changes have become tangible. For example, when prostate cancer is treated in radiation therapy, a shape of the urinary bladder in the vicinity of the prostate changes depending an amount of urine and, likewise, a shape of the rectum in the vicinity of the prostate changes depending an amount of gas inside. Therefore, even when the size of the prostate does not change a shape thereof may change accordingly. Also, with head and neck cancer, the size of the cancer itself changes due to effects of radiation therapy and thus a cancer rendered in a CT image as of planning a treatment plan may be largely different from that in a three-dimensional image imaged for alignment.

In actual treatment, alignment of three-dimensional images includes automatic alignment by a system installed with an image alignment function and manual alignment where an operator performs alignment manually while watching an image. Generally, automatic alignment is executed first and then a result therefrom is corrected by manual alignment in a procedure. The automatic alignment is to determine six degrees of freedom for bed positioning with an evaluation function implemented in a system. However, the evaluation functions conventionally used have constant determination criteria for alignment and align positions of the entire images. Therefore, it may be difficult to perform alignment corresponding to changes of shape or displacement of the target or organ at risk for every treatment. On the other hand, in manual alignment, it is possible to perform alignment using a region of interest of the operator as a reference. However, the criteria is dependent on the operator and thus an alignment result varies and a degree how much to consider changes of shape or displacement of the target or organ at risk for every treatment is also dependent on the operator. Therefore, it is assumed that bed positioning with a high accuracy is difficult.

With such changes with the target or organ at risk for every treatment, conventionally, a treatment plan sets those changes as a margin. For example with a target, a doctor sets a region to treat (clinical target volume (CTV)) and sets a region to actually treat based on CTV while considering a certain margin (planning target volume (PTV)). The degree of the margin to set is different for every facility in the present situation although there is a guideline by the academic society or the like. Therefore, when this margin is larger PTV also becomes larger and so does an irradiation region of radioactive rays. Thus, it is desired to set a margin with least excess as possible.

Furthermore, three dimensional radiation therapy is increasingly used where radioactive rays are focused on a tumor region (affected part) while imparting dose to nearby organs in the vicinity of the tumor region is avoided as much as possible. This includes, for example, intensity modulated radiation therapy (IMRT) or radiation therapy using particle beams. In order to irradiate such a target with focused dose, bed positioning and image alignment with a higher accuracy are desired.

In bed positioning using a treatment plan CT image and three-dimensional image of a patient in a radiation therapy system including such a three-dimensional tomographic imaging device, a region of interest in radiation therapy such as a target or organ at risk is rendered, which may have been difficult in positioning using the conventional projection images. Therefore, there is an advantage that alignment with reference to the above is enabled.

When a three-dimensional image is used, there is an advantage that a region of interest such as a target or organ at risk is rendered. It is desired that the same state as of planning of a treatment plan is reproduced upon positioning for every treatment; however, their shapes or positions actually change and thus positioning considering these changes is required.

For these changes of shapes or positions, the aforementioned PTL 1 describes a method to compare and analyze shapes of a patient in a treatment plan image and positioning image, to calculate a displacement amount of a bed based on the result, and to move the bed. This literature describes analysis of a shape in an image; however, changes of inner shapes due to forces applied externally or a posture at the time of treatment are estimated by modeling interior organs by defining a spring model. Therefore, cases may be assumed where especially influence by inner tissues or changes in shapes or positions of a region of interest such as a target or organ at risk in an image for every treatment are not always calculated clearly. Moreover, this literature does not describe a means to accumulate a parameter as an analysis result calculated for every treatment nor a means to utilize those accumulated parameters.

Changes of shapes or positions of a target or organ at risk for every treatment have been handled by setting a margin to a treatment region based on past experiences of an operator or the like. In actual treatment, however, changes of shapes or positions cannot be calculated with a high accuracy or accumulated and those changes are not utilized in treatment, which are the original problems.

Therefore, in consideration of the above points, the present invention aims at providing a radiation therapy apparatus, system and positioning method capable of calculating and/or accumulating, for every treatment, shapes or position changes of a region of interest such as a target or organ at risk in an image and performing bed positioning with a high accuracy in radiation therapy.

Solution to Problem

A first solution of the present invention provides a radiation therapy apparatus including an image processing unit and a display unit, where the image processing unit inputs, thereto, a treatment plan image imaged in advance as a tomographic image and information of a region of interest including a target and/or an organ at risk generated by a treatment planning device and inputs, thereto, a positioning image imaged by a tomographic imaging device for positioning for irradiation of radioactive rays, performs alignment of the treatment plan image and the positioning image, calculates a first deformation parameter and a second deformation parameter representing deformation in a whole image and deformation in a partial image, respectively, between the aligned treatment plan image and the positioning image and calculates a displacement amount parameter representing displacement from the region of interest in the treatment plan image to the region of interest in the positioning image, calculates a positioning parameter representing a position displacement amount and rotation amount of a bed based on the first and second deformation parameters and the displacement amount parameter, displays one or more of an image representing the first deformation parameter, an image representing the second deformation parameter, an image representing the displacement amount parameter, and an image representing the positioning parameter on the display unit, and outputs the positioning parameter to cause the bed to move and rotate.

A second solution of the present invention provides a radiation therapy system including a treatment planning device for generating a treatment plan image imaged in advance as a tomographic image in order to produce a treatment plan of radiation therapy and information of a region of interest including a target and/or an organ at risk, a tomographic imaging device for generating, as a tomographic image, a positioning image for positioning of an object of irradiation of radioactive rays, and a positioning system, including an image processing unit and a display unit, for executing bed positioning processing, where the image processing unit in the positioning system inputs, thereto, a treatment plan image generated by a treatment planning device and information of a region of interest and inputs, thereto, the positioning image imaged by the tomographic imaging device for positioning, performs alignment of the treatment plan image and the positioning image, calculates a first deformation parameter and a second deformation parameter representing deformation in a whole image and deformation in a partial image, respectively, between the aligned treatment plan image and the positioning image and calculates a displacement amount parameter representing displacement from the region of interest in the treatment plan image to the region of interest in the positioning image, calculates a positioning parameter representing a position displacement amount and rotation amount of a bed based on the first and second deformation parameters and the displacement amount parameter, displays one or more of an image representing the first deformation parameter, an image representing the second deformation parameter, an image representing the displacement amount parameter, and an image representing the positioning parameter on the display unit, and outputs the positioning parameter to cause the bed to move and rotate.

A third solution of the present invention provides a positioning method in a radiation therapy apparatus where the radiation therapy apparatus includes an image processing unit and a display unit, where the image processing unit inputs, thereto, a treatment plan image imaged in advance as a tomographic image and information of a region of interest including a target and/or an organ at risk generated by a treatment planning device and inputs, thereto, a positioning image imaged by a tomographic imaging device for positioning for irradiation of radioactive rays, performs alignment of the treatment plan image and the positioning image, calculates a first deformation parameter and a second deformation parameter representing deformation in a whole image and deformation in a partial image, respectively, between the aligned treatment plan image and the positioning image and calculates a displacement amount parameter representing displacement from the region of interest in the treatment plan image to the region of interest in the positioning image, calculates a positioning parameter representing a position displacement amount and rotation amount of a bed based on the first and second deformation parameters and the displacement amount parameter, displays one or more of an image representing the first deformation parameter, an image representing the second deformation parameter, an image representing the displacement amount parameter, and an image representing the positioning parameter on the display unit, and outputs the positioning parameter to cause the bed to move and rotate.

Advantageous Effects of Invention

The present invention allows for providing a radiation therapy apparatus, system and positioning method capable of calculating and/or accumulating, for every treatment, shapes or position changes of a region of interest such as a target or organ at risk in an image and performing bed positioning with a high accuracy in radiation therapy.

BRIEF DESCRIPTION OF DRAWINGS

FIG. 9 is a diagram illustrating an outline of a displacement amount parameter of an embodiment of the radiation therapy system of the present invention.

DESCRIPTION OF EMBODIMENTS

1. Summary

The present embodiment provides, for example, a treatment planning device for producing a treatment plan of radiation therapy, an image server for storing the treatment plan image, a tomographic imaging device for imaging a tomographic image for positioning of an object for irradiation of radioactive rays, a bed for a patient to lie down on, and a positioning system for performing positioning of the bed, where an image processing unit for processing the treatment plan image stored in the image server and the tomographic positioning image imaged by the tomographic imaging device includes an image alignment unit for performing image alignment, a region extraction unit for extracting regions from the treatment plan image and the positioning image, a region conversion unit for converting a region based on an alignment parameter obtained from the image alignment unit, a deformation parameter calculation unit for calculating a deformation parameter from the regions extracted by the region extraction unit, a deformation parameter evaluation unit for evaluating the deformation parameter, and a displacement amount parameter calculation unit for calculating a displacement amount parameter from the extracted regions, the positioning system including a deformation parameter database for storing the deformation parameter as a processing result from the image processing unit, a displacement amount parameter database for storing the displacement amount parameter, an extracted region database for storing the extracted regions, and a display unit for displaying a result from the image processing unit.

2. Radiation Therapy System

Figure 1:
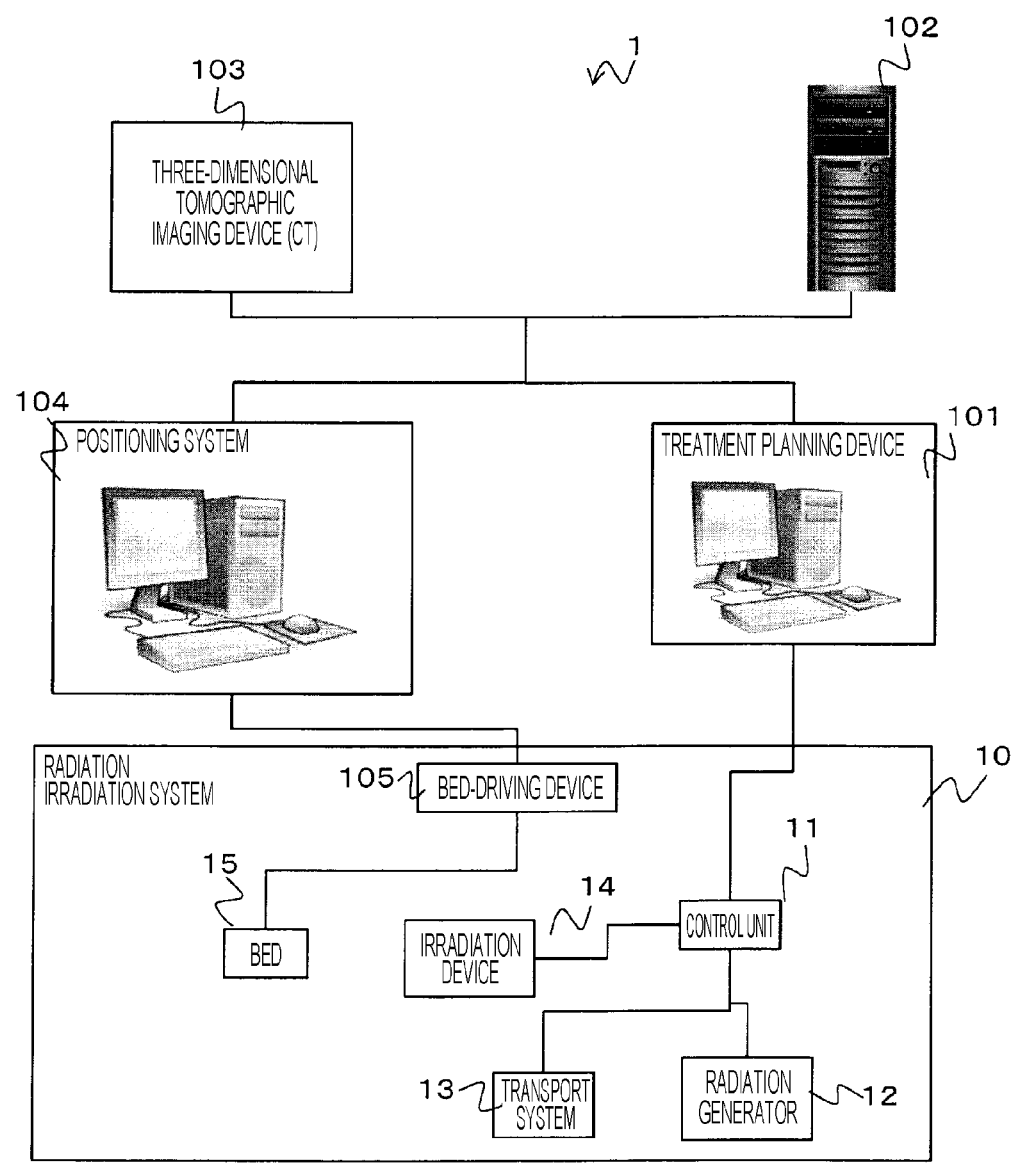
FIG. 1 is a schematic diagram illustrating an exemplary configuration of an embodiment of a radiation therapy system of the present invention.

Embodiments of a radiation therapy system of the present invention will be described with FIGS. 1 to 10. In FIG. 1, a radiation therapy system 1 mainly includes a radiation irradiation system 10, a treatment planning device 101, an image server 102, a three-dimensional tomographic imaging device 103, and a positioning system 104. The radiation irradiation system 10 mainly includes a radiation generator 12 for generating radioactive rays, a transport system 13 for transporting the radioactive rays generated by the radiation generator 12 to an irradiation device 14, the irradiation device 14 including an irradiation head (irradiation nozzle), gantry, or the like for emitting the radioactive rays, a control unit 11 for controlling the radiation generator 12, transport system 13, irradiation device 14, and the like, a bed 15 for a patient to lie down on, and a bed-driving device 105. The gantry in the irradiation device 14 generally includes a rotation mechanism and thus is capable of arbitrarily changing an irradiation direction of therapeutic radioactive rays by rotating this rotary gantry.

Figure 2:
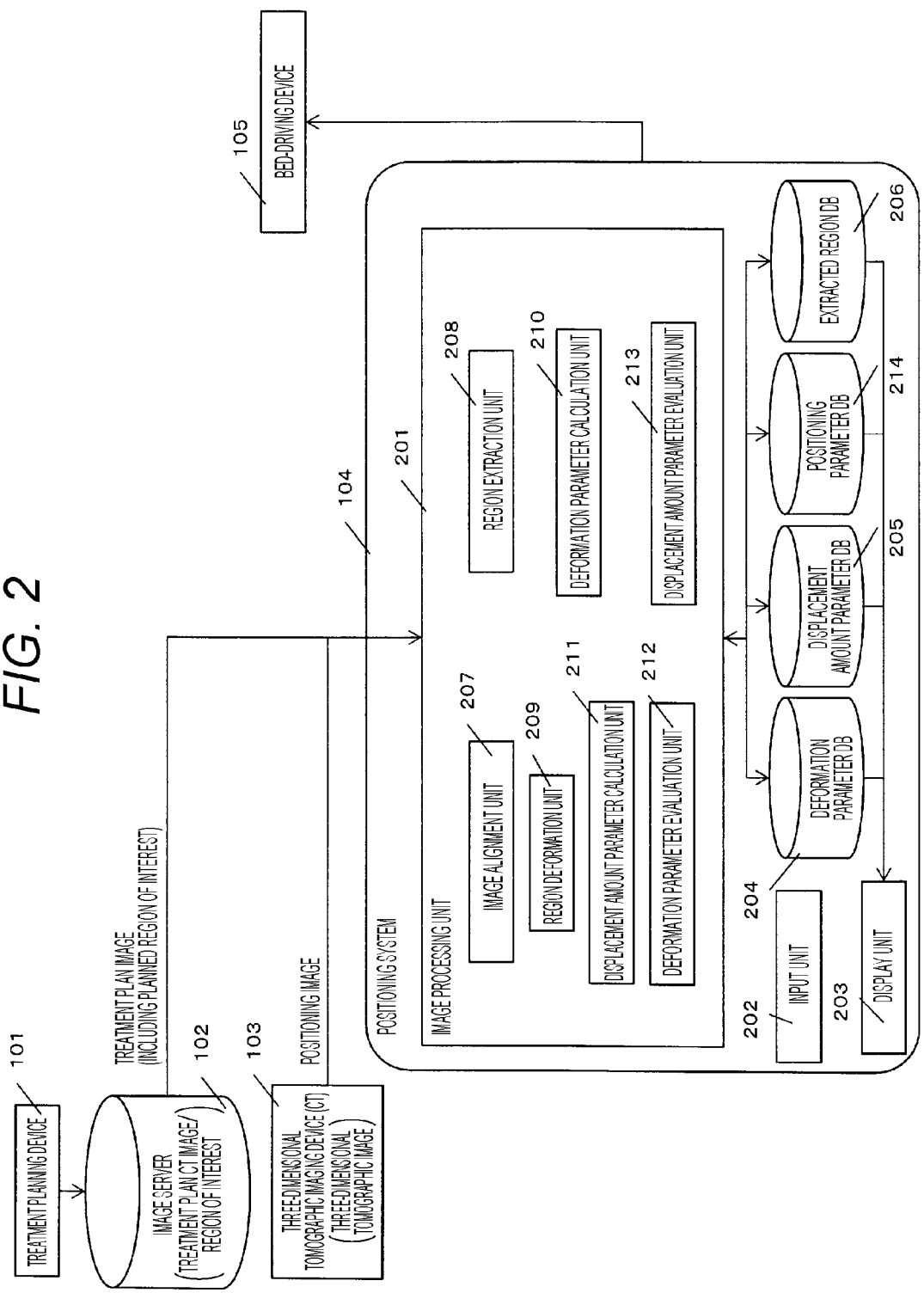
FIG. 2 is a diagram illustrating an exemplary system configuration of an alignment system and related configuration of an embodiment of the radiation therapy system of the present invention.

FIG. 2 is a diagram illustrating an exemplary system configuration of an alignment system and related configuration of an embodiment of the radiation therapy system of the present invention. Configurations for deforming or calculating a position of a region of interest such as a target or organ at risk during treatment for utilization in positioning of the present embodiment will be described with FIG. 2. The treatment planning device 101 includes therein a device for producing a treatment plan of radiation therapy. The treatment planning device 101 further sets, to a treatment plan CT image (treatment plan image), a region of interest (planned ROI) which is a region important in radiation therapy such as a treatment target region or organ at risk. The treatment planning device 101 is connected to the image server 102 via a network.

The image server 102 stores the treatment plan CT image used in planning of the treatment plan in the treatment planning device 101 or information related to the region of interest such as the target or organ at risk having been set upon creation of the treatment plan. Communication or storage of such images and information via a network can be easily implemented by using, for example, the digital image and communication of medicine (DICOM) format generally used in the medical field. The three-dimensional tomographic imaging device 103 acquires a three-dimensional tomographic image (CT, positioning image) of a patient on the bed 15. This three-dimensional tomographic imaging device 103 includes, specifically, a cone beam CT device mounted on the gantry in the radiation irradiation system 10 or a CT device installed in the same room as the irradiation device 14. The three-dimensional tomographic image obtained by the three-dimensional tomographic imaging device 103 can be communicated via a network using the aforementioned DICOM format.

The positioning system 104 is capable of acquiring each of the treatment plan CT image and region of interest used in the treatment plan in the treatment planning device 101 from the image server 102 and the three dimensional tomographic image from the three-dimensional tomographic imaging device 103 via a network. The positioning system 104 is further connected to the bed-driving device 105 (bed position control device) in the radiation therapy system 10 and move and rotates the bed 15 to a predetermined position by transmitting a positioning parameter calculated by the positioning system 104 to the bed-driving device 105 and prepares for performing treatment. The positioning parameter is a parameter representing a position displacement amount and rotation amount of the bed and can be calculated using a deformation parameter and displacement amount parameter (details will be described later). Incidentally, "position displacement amount and rotation amount" with regard to bed positioning may be herein simply referred to as "displacement amount". Moreover, "displacement distance and displacement direction" with regard to the displacement amount parameter may be simply referred to as "displacement amount".

This positioning system 104 includes an image processing unit 201, an input unit 202 where an operator carries out input operation, a display unit 203 for displaying a result of image processing, a deformation parameter database 204 for storing the deformation parameter obtained as a result of the image processing, a displacement amount parameter database 205 for storing the displacement amount parameter obtained in a similar manner, an extracted region database 206 obtained in a similar manner, and a positioning parameter database 214. The image processing unit 201 includes an image alignment unit 207 for performing alignment of the treatment plan image and positioning image, a region extraction unit 208 for extracting a region of interest such as a target or organ at risk from the treatment plan image, and positioning image, a region deformation unit 208 for deforming the planned ROI having been set to the treatment plan image using the deformation parameter obtained from the image alignment 207, a deformation parameter calculation unit 210 for calculating the deformation parameter in a region extracted by the region extraction unit 208, a deformation parameter evaluation unit 212 for evaluating the deformation parameter and previous deformation parameters, a displacement amount parameter calculation unit 211 for calculating a displacement amount parameter from regions calculated by the region extraction unit 208 and region deformation unit 209, and a displacement amount parameter evaluation unit 213 for evaluating the displacement amount parameter and previous displacement amount parameters. The input unit 202 is a means to provide an instruction to the positioning system 201 via a user interface displayed on the display unit 203 and generally includes a key board, mouse, or the like. Moreover, a graphical user interface (GUI) is often used as the user interface. The display unit 203 displays a result of aligning the treatment plan CT image stored in the image server 102 and the three-dimensional tomographic image imaged by the three-dimensional tomographic imaging device 103 and thereby provides information for making a decision as to whether positioning has been performed correctly to medical staff or the like, thus allowing for easy decision on the result of alignment.

The bed-driving device 105 is a control device for controlling the bed 15 where an irradiation target to irradiate with radioactive rays lies down on. The bed-driving device 105 has functions to receive a displacement amount of the bed 15 (positioning parameter) calculated by the positioning system 104 and to transmit a displacement instruction to a driving mechanism included in the bed 15. The bed 15 and bed-driving device 105 form a part of the radiation irradiation system 10.

3. Positioning Processing

Figure 3:
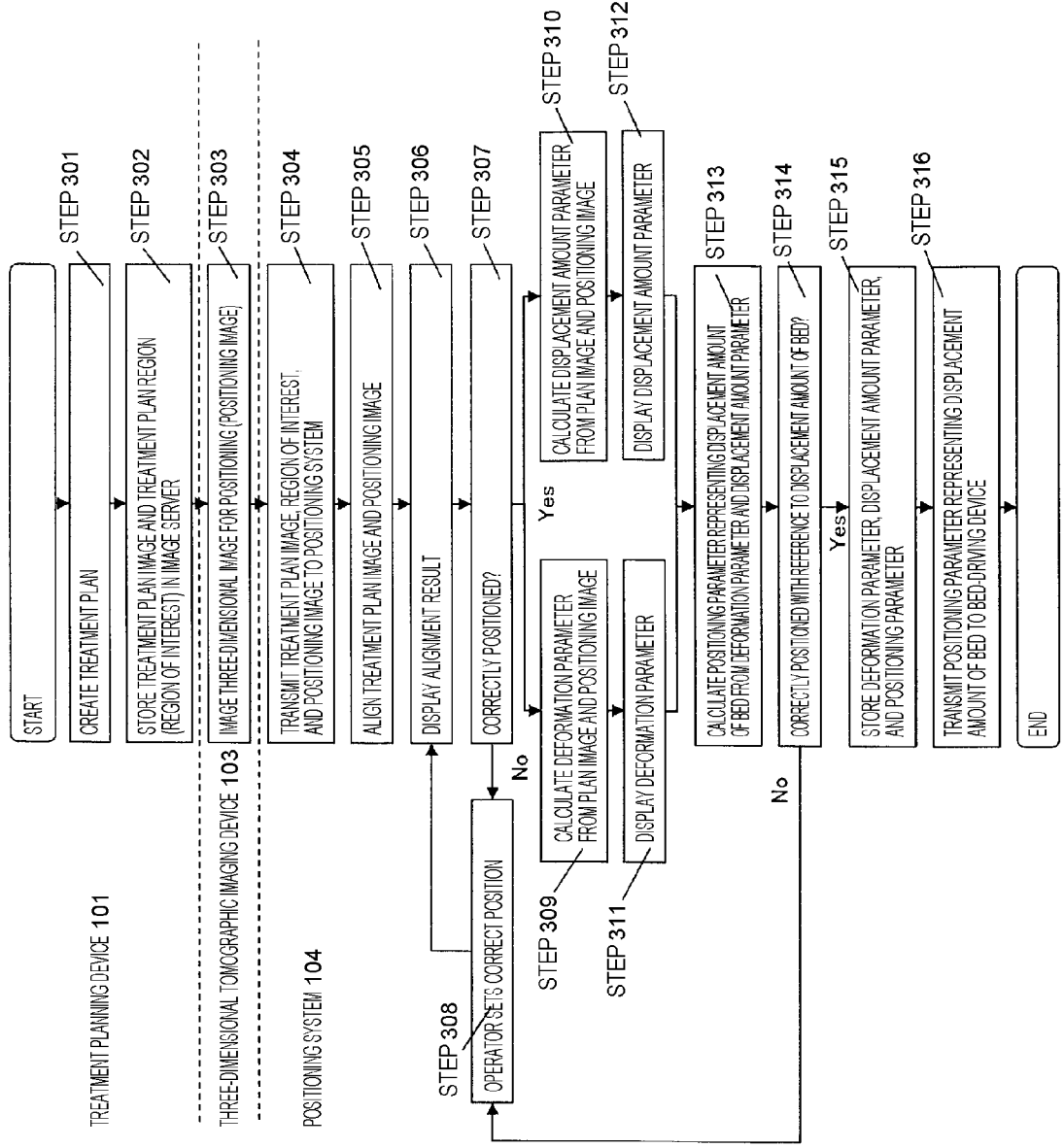
FIG. 3 is a diagram illustrating an exemplary flow of bed positioning of an embodiment of the radiation therapy system of the present invention.

FIG. 3 is a diagram illustrating an exemplary flow of bed positioning of an embodiment of the radiation therapy system of the present invention. A flow of positioning processing by the alignment system of the radiation therapy system as illustrated in FIG. 2 and systems related thereto will be described with FIG. 3. Incidentally, the treatment plan CT image or the region of interest (planned ROI) such as the target or organ at risk is generated in the treatment planning device 101 and accumulated in the image server 102. Also, the three-dimensional tomographic image is generated by the three-dimensional tomographic imaging device 103. The image data and data of the region of interest are used by the positioning system 104 via a network.

In FIG. 3, the treatment planning device 101 first reads the treatment plan CT image for planning of the treatment plan from the image server 102 via a network. Incidentally, the treatment plan CT image is imaged in advance by the three-dimensional tomographic imaging device 103 or another imaging device and stored in the image server 102. Thereafter, the treatment planning device 101 sets an irradiation region to the irradiation target by a function to set which region to irradiate. Furthermore, the treatment planning device 101 calculates from which direction and how to irradiate the set irradiation region with radioactive rays based on the instruction from the operator and produces the treatment plan. Here, a region (planned ROI) of high interest in radiation therapy such as the target and organ at risk are also set together with the irradiation region (step 301). The treatment planning device 101 outputs this data on the set irradiation region or planned ROI to the image server 102 via a network and stores the data in the image server 102 together with the treatment plan CT image (step 302). The above is substantially the same as a procedure for a general treatment plan.

In radiation therapy, it is required to match the irradiation target having been set to a tumor in the patient with the center point of irradiation before irradiating the irradiation target with radioactive rays and therefore bed positioning is performed before initiation of treatment. Hereinafter, bed positioning will be described. First, the three-dimensional tomographic imaging device 103 images the three-dimensional tomographic image while the patient is stable on the bed 15 (step 303). Here, there are cases where the three-dimensional tomographic image is imaged by moving the bed based on visual measurement using, as a marker, an optical device such as a laser marker and a marker such as a sticker or cross lines attached to or drew on the patient in advance such that the target in the patient approaches near the center point of irradiation.

Next, the positioning system 104 receives the treatment plan CT image and information of the region of interest (planned ROI) such as the target or organ at risk planned in the treatment planning device 101 and the three-dimensional tomographic image for positioning imaged by the three-dimensional tomographic imaging device 103 via a network (step 304). Next, in the positioning system 104 the transmitted treatment plan CT image and three-dimensional tomographic image are transmitted to the image processing unit 201. The image processing unit 201 performs alignment using an evaluation expression having been determined in the image alignment unit 207 in advance (step 305). As this evaluation expression, for example, a method to maximize mutual information that is widely known in the field of image alignment is used. The method to maximize mutual information is a method to calculate to search for a position where information quantities are calculated while two images are subjected to variations in six degrees of freedom in displacement and rotation, search for a position where the values are the largest, and to determine that such a case is most properly aligned.

Next, the image processing unit 201 displays the alignment result determined by the image alignment unit 207 on the display unit 203 (step 306). The operator determines as to whether the result has been successful and inputs the result to the image processing unit 201 via the input unit 202 (step 307). When alignment has been performed correctly, the image processing unit 201 can obtain positioning parameters for positional relationship between the treatment plan CT image and three-dimensional tomographic image, namely the six degrees of freedom in displacement and rotation, by known image processing. On the contrary, when the position is incorrect, the operator corrects the position by inputting a correct position using the input unit 202 while watching the treatment plan CT image and three-dimensional tomographic image. The image alignment unit 207 can obtain the positioning parameters for the six degrees of freedom which are positional relationship between the treatment plan CT image and three-dimensional tomographic image based on the corrected position when recognizing the correction (step 308). The above is a procedure for general bed positioning. The positioning system 104 transmits the positioning parameters for the six degrees of freedom obtained as described above to the bed-driving device 105 (step 316), whereby positioning ends.

The present embodiment is further added with processing where the positioning system 104 calculates the deformation parameter and displacement amount parameter based on the alignment result of the treatment plan CT image (treatment plan image) and three-dimensional image (image for positioning), compares with previous respective parameters (which may be excluded in the first treatment), and evaluates the positioning result. Hereinafter an outline of the processing will be described.

The deformation parameter evaluation unit 212 of the image processing unit 201 calculates the deformation parameter from the treatment plan image and positioning image with which the operator has once confirmed the positioning result (step 309) and displays the deformation parameter (step 311). Details of this processing will be described later. Meanwhile, a displacement amount parameter calculation unit 211 of the image processing unit 201 calculates the displacement amount parameter from the treatment plan image and positioning image with which the operator has likewise confirmed the positioning result (step 310). The displacement amount parameter is also displayed on the display unit 203 (step 312). Details of this processing will be also described later. Based on the deformation parameter and displacement amount parameter calculated and displayed on the display unit 203, the deformation parameter evaluation unit 212 and displacement amount parameter evaluation unit 213 calculates the positioning parameter representing a displacement amount of the bed (step 313). Furthermore, the image processing unit 201 may display the positioning parameter on the display unit 203. The operator determines whether positioning is correct (step 314). When positioning is determined as correct, positioning parameters for the aforementioned six degrees of freedom are determined and the image processing unit 201 stores the deformation parameter and displacement amount parameter in the deformation parameter DB 204 and displacement amount parameter DB 205, respectively, and stores the positioning parameters in the positioning parameter DB 214 (step 315). On the other hand, when positioning is determined as incorrect, the image processing unit 201 returns to step 308 and repeats processing from step 308 to step 315. When positioning is determined as correct lastly, the image processing unit 201 calculates positioning parameters for the six degrees of freedom based on the deformation parameter and displacement amount parameter and transmits the parameters to the bed-driving device (step 316), whereby positioning ends.

Incidentally, the image processing unit 201 can display one or more of the deformation parameter, displacement amount parameter, and positioning parameters on the display unit 203 as appropriate by appropriately reading the deformation parameter and displacement amount parameter from the deformation parameter DB 204 and displacement amount parameter DB 205, respectively, and reading the positioning parameters from the positioning parameter DB 214 based on an instruction from the input unit 202 or the like.

Figure 4:
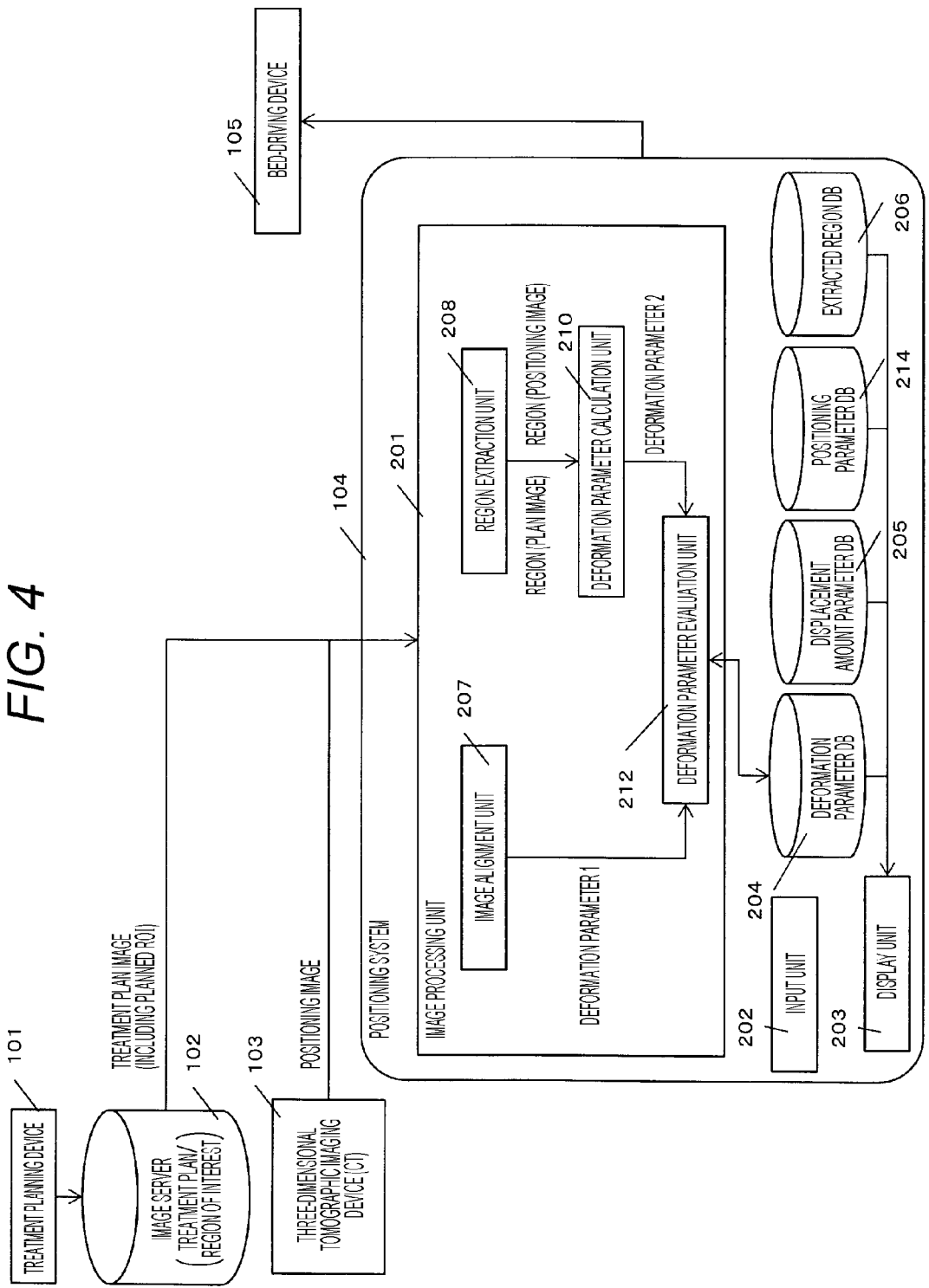
FIG. 4 is a diagram illustrating an exemplary system configuration of a configuration for obtaining a deformation parameter of an embodiment of the radiation therapy system of the present invention.
Figure 5:
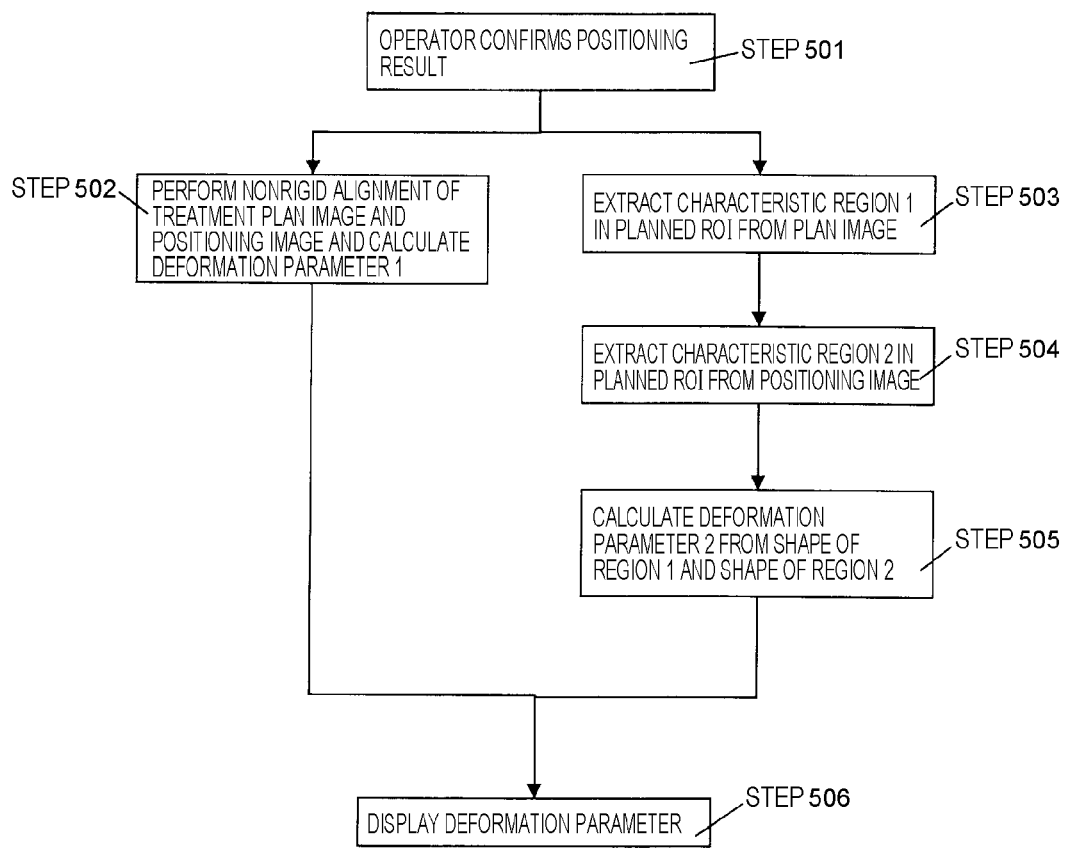
FIG. 5 is a diagram illustrating an exemplary flow for obtaining a deformation parameter of an embodiment of the radiation therapy system of the present invention.
Figure 6:
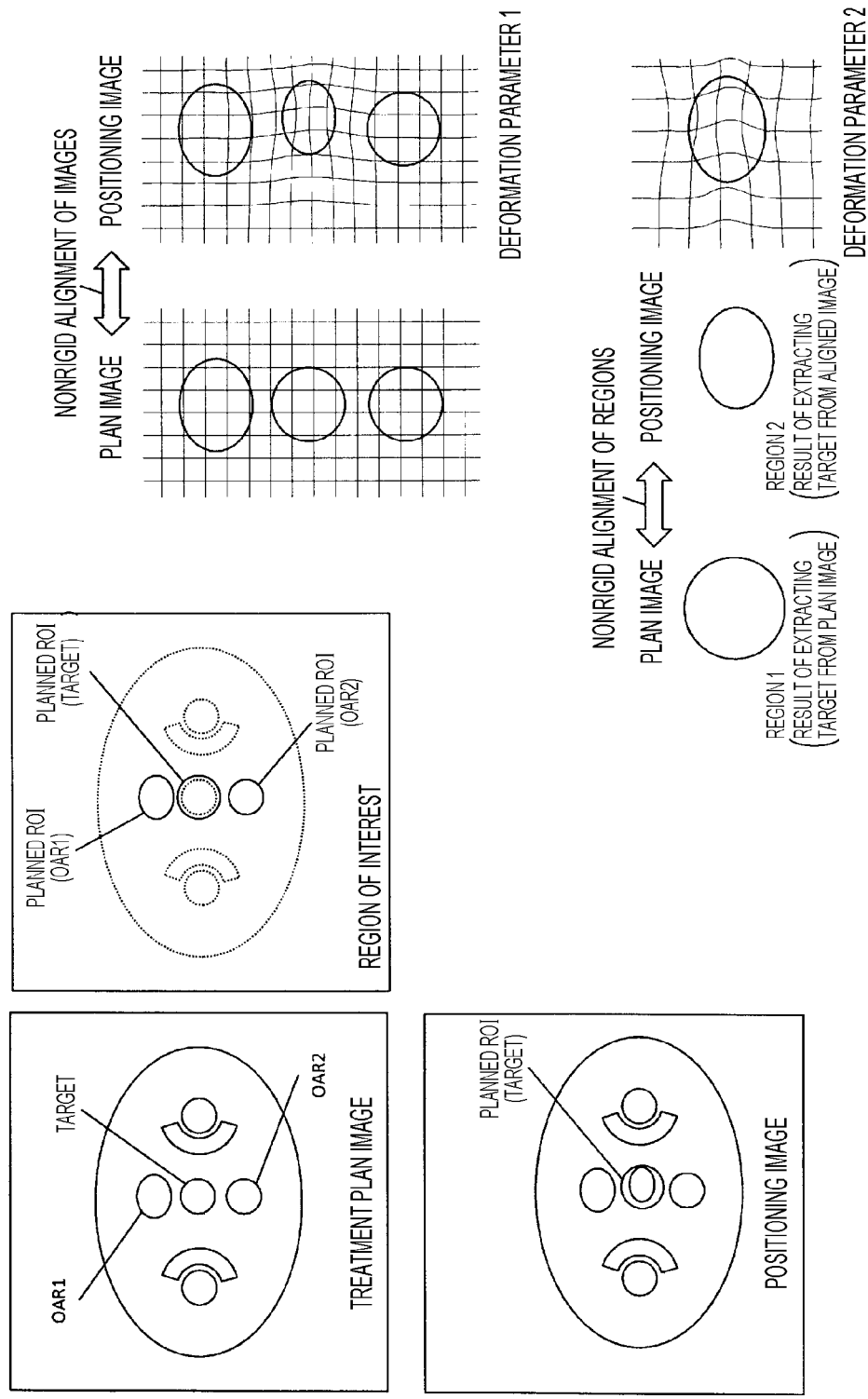
FIG. 6 is a diagram illustrating an outline of a deformation parameter of an embodiment of the radiation therapy system of the present invention.

FIG. 4 is a diagram illustrating an exemplary system configuration of a configuration for obtaining a deformation parameter of an embodiment of the radiation therapy system of the present invention. FIG. 5 is a diagram illustrating an exemplary flow for obtaining the deformation parameter and FIG. 6 is a diagram illustrating an outline of the deformation parameter. Next, processing for calculating the deformation parameter in the image processing unit 201 (steps 309 and 311) will be described in detail with FIGS. 4 to 6.

First, the operator confirms the alignment result of the treatment plan image and positioning image displayed on the display unit 203 and determines positioning as correct (step 501). In the image processing unit 201, the image alignment unit 207 calculates the deformation parameter based on the aligned treatment plan image and positioning image using a non-rigid registration method (step 502). This non-rigid registration method includes, for example, the demon algorithm or methods such as a B-spline method and may be any method. For example, using a B-spline method as a method of deformation and using mutual information as the evaluation expression for alignment allows for calculating the deformation parameter representing the degree of deformation of the entire positioning image relative to the treatment plan image. This outline is illustrated in FIG. 6. A grid on a lattice in the treatment plan is deformed by using the aforementioned non-rigid registration method, thereby allowing for obtaining a deformation parameter 1.

Meanwhile, the image processing unit 201 applies (arranges or specifies) the planned ROI having been set as of planning the treatment plan to the treatment plan image and positioning image aligned by the operator. The region extraction unit 208 then extracts a characteristic region (region 1) within this range first in the treatment plan image (step 503). In the image processing unit 201, the region extraction unit 208 also extracts a characteristic region (region 2) in the planned ROI in the positioning image (step 504). In the image processing unit 201 the deformation parameter calculation unit 210 calculates the deformation parameter 2 for these extracted region 1 and region 2 (step 505). As illustrated in FIG. 6, a difference between the deformation parameter 1 and deformation parameter 2 is that the deformation parameter 1 is calculated for the entire image while the deformation parameter is obtained for the extracted region. The image processing unit 201 displays the obtained deformation parameter 1 and deformation parameter 2 on the display unit 203 (step 506). The calculated deformation parameters can be represented by appropriate data such as a group of coordinates of lattice points or a group of moving vectors of lattice points.

Figure 7:
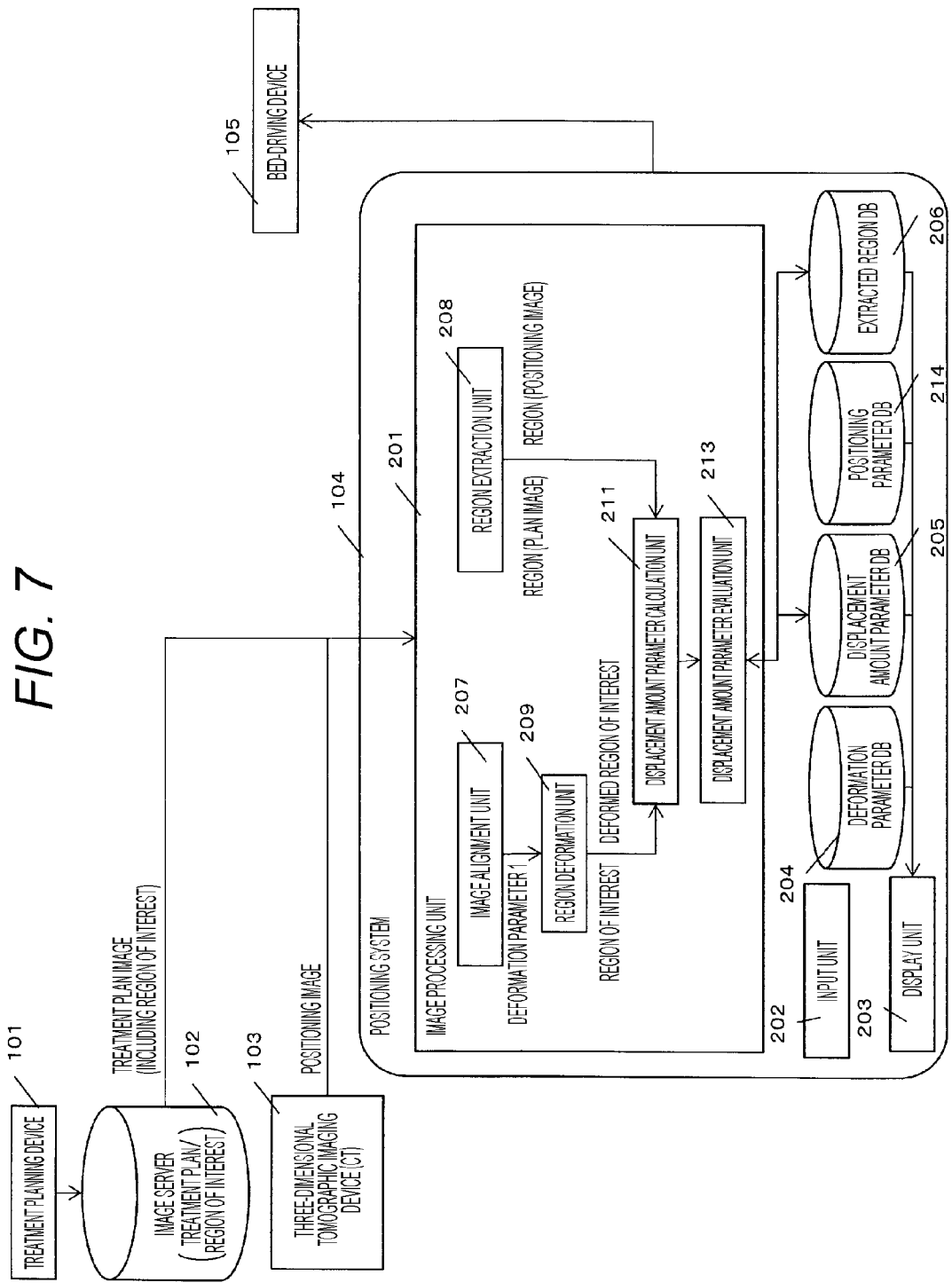
FIG. 7 is a diagram illustrating an exemplary system configuration of a configuration for obtaining a displacement amount parameter of an embodiment of the radiation therapy system of the present invention.
Figure 8:
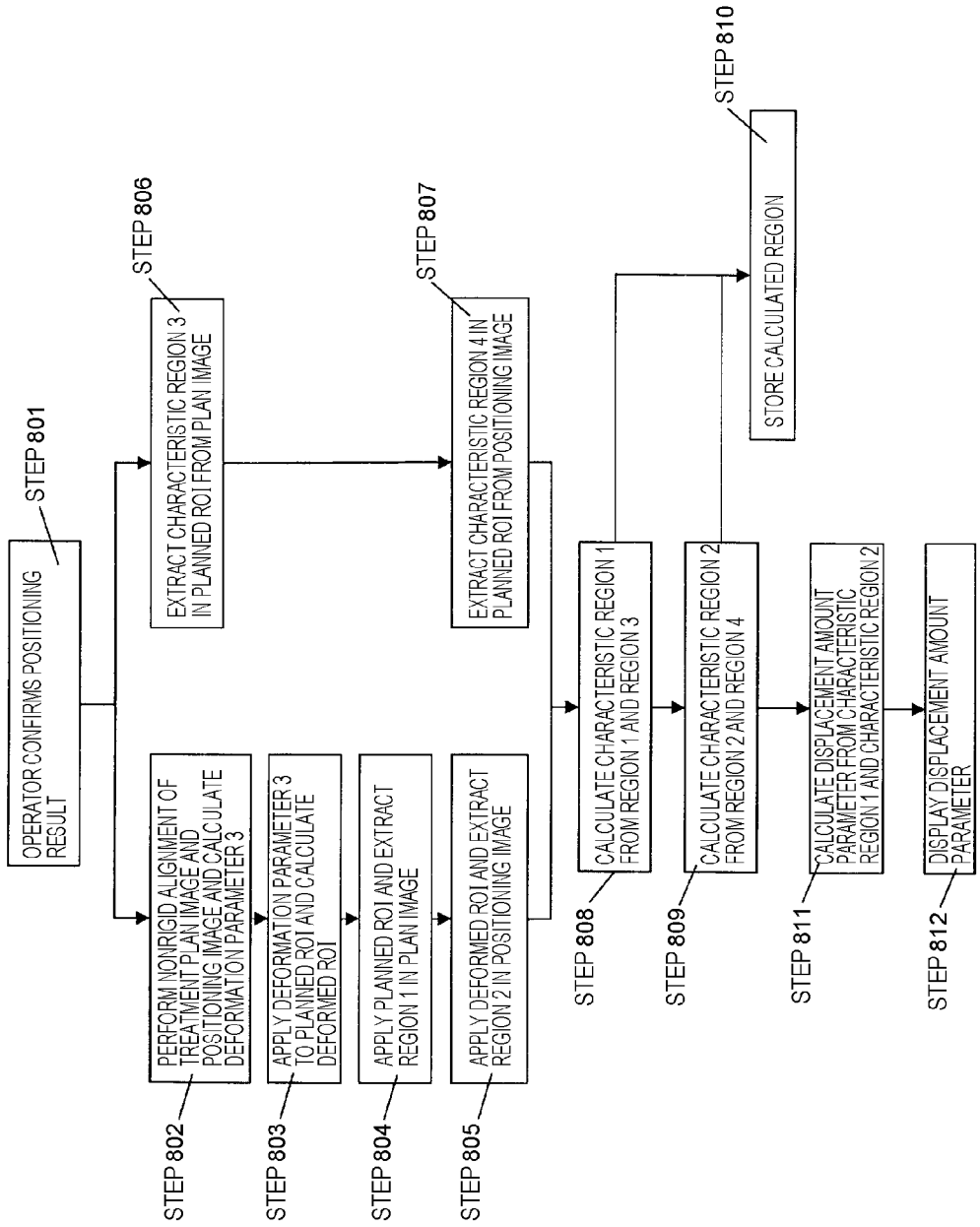
FIG. 8 is a diagram illustrating an exemplary flow for obtaining a displacement amount parameter of an embodiment of the radiation therapy system of the present invention.

FIG. 7 is a diagram illustrating an exemplary system configuration of a configuration for obtaining a displacement amount parameter of an embodiment of the radiation therapy system of the present invention. FIG. 8 is a diagram illustrating an exemplary flow for obtaining the displacement amount parameter and FIG. 9 is a diagram illustrating an outline of the displacement amount parameter. Next, processing for calculating the displacement amount parameter in the image processing unit 201 (steps 310 and 312) will be described in detail below with FIGS. 7 to 9.

First, the operator confirms the alignment result of the treatment plan image and positioning image displayed on the display unit 203 and determines positioning as correct (step 801). In the image processing unit 201, the image alignment unit 207 calculates a deformation parameter 3 based on the aligned treatment plan image and positioning image using a non-rigid registration method (step 802). This non-rigid registration method is similar to the method described in step 502. Incidentally, the image processing unit 201 may read the deformation parameter 1 calculated in step 502 from the deformation parameter DB 204 as the deformation parameter 3 instead of step 801 and use the deformation parameter 1 as the deformation parameter 3. In the image processing unit 201 the region deformation unit 209 applies the obtained deformation parameter 3 to the planned ROI in the treatment plan image and calculates a deformed ROI (step 803). Next, the image processing unit 201 applies the planned ROI in the treatment plan image and extracts the region (region 1) corresponding to the planned ROI (804). Furthermore, the image processing unit 201 applies the deformed planned ROI in the positioning image and extracts the region (region 2) corresponding to the deformed planned ROI (step 805).

Meanwhile, in the image processing unit 201, the region extraction unit 208 illustrated in FIG. 7 extracts a characteristic region (region 3) in the planned ROI set in the treatment plan image (step 806). The image processing unit 201 further arranges the planned ROI set in the treatment plan image over the positioning image and extracts a characteristic region (region 4) in the planned ROI (step 807).

The image processing unit 201 calculates a characteristic region 1 representing a common region to the region 1 and region 3 that are regions in the treatment plan image (step 808). The image processing unit 201 further calculates a characteristic region 2 representing a common region to the region 2 and region 4 that are regions in the positioning image (step 809). The image processing unit 201 stores the extracted regions 1 to 4 and characteristic region 1 and characteristic region 2 in the extracted region DB 206 (step 810). The image processing unit 201 calculates the displacement amount parameters for the characteristic region 1 and characteristic region 2 (step 811). Furthermore, the image processing unit 201 displays the calculated displacement amount parameter on the display unit 203 (step 812).

The aforementioned extraction of regions will be described in detail with FIG. 9. It is assumed that the treatment plan image (treatment plan CT image) renders the target as an object of treatment and organ at risk (hereinafter referred to as OAR). The treatment plan image includes a planned ROI (target), planned ROI (OAR 1), and planned ROI (OAR 2) having been set upon planning in the treatment planning device 101. Meanwhile, although the positioning image imaged for every treatment renders the target and OAR, shapes thereof are not always the same and likewise relative positions thereamong are not always the same. Therefore, the image processing unit 201 first sets the planned ROI in the treatment plan image and extracts the region (region 1) in the planned ROI. The image processing unit 201 calculates the deformation parameter 3 based on the aforementioned treatment plan image and positioning image similarly to the non-rigid registration method. The image processing unit 201 deforms the planned ROI in the treatment plan image using the deformation parameter 3, applies the deformed planned ROI to the positioning image, and extracts a region (region 2) in the planned ROI. Meanwhile, the image processing unit 201 extracts the target region (region 3) in the treatment plan image using a predetermined region extraction algorithm as appropriate. The image processing unit 201 further extracts the target region (region 4) in the positioning image using, likewise, a predetermined region extraction algorithm as appropriate. These extractions can be performed with a higher accuracy by performing within a region in the planned ROI set to the treatment plan image. In this manner, the region 1 and region 3 extracted from the treatment plan image and the region 2 and region 4 extracted from the positioning image are regions related to the target extracted from each of the images. Therefore, the image processing unit 201 calculates, as a composite region thereof (for example a part or all of a common region), a common region obtained by means of, for example, logical add or the like of the region 1 and region 3 as the characteristic region 1 and a common region of the region 2 and region 4 as the characteristic region 2. The image processing unit 201 determines a characteristic point, for example a centroid for each of the characteristic region 1 and characteristic region 2 and calculates a distance and displacement direction therebetween as the displacement amount parameter. Incidentally, the displacement amount parameter can be represented as a vector.

In FIG. 9, the aforementioned characteristic regions have been described using logical add; however, these may be regions of common parts (logical multiply). Also, as the characteristic point of the characteristic region, a centroid has been used in the description; however, a distance and displacement direction obtained from comparison of contour outlines may be used as the displacement amount parameters.

Figure 10:
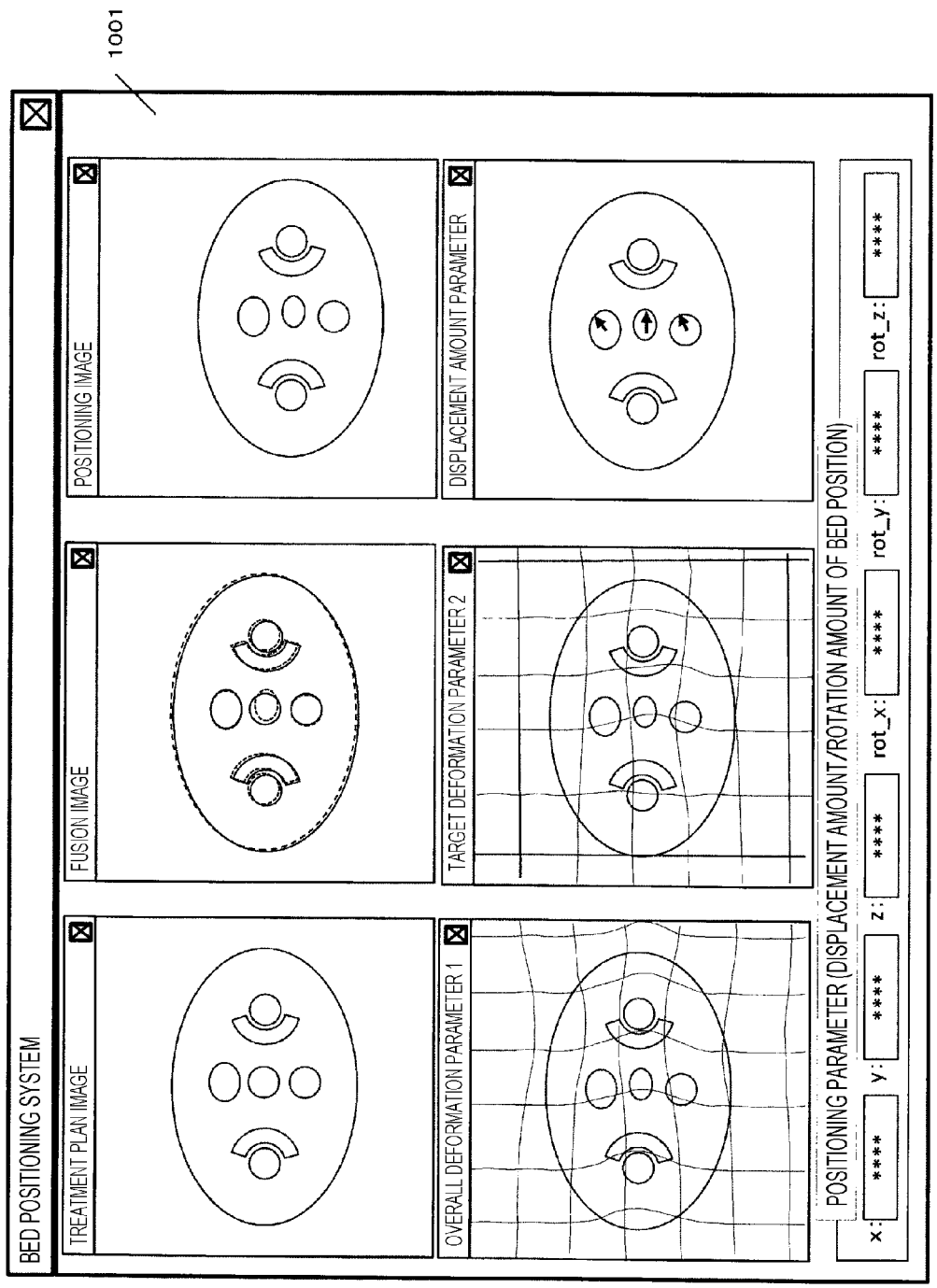
FIG. 10 is a diagram illustrating an exemplary screen for displaying a deformation parameter and displacement amount parameter of an embodiment of the radiation therapy system of the present invention.

FIG. 10 is a diagram illustrating an exemplary screen for displaying the deformation parameter, displacement amount parameter, and positioning parameter obtained by the positioning system 201. Conventionally, only a treatment plan image, positioning image, and a fusion image displaying an overlapping image thereof are displayed on the display unit 203; however, the deformation parameter and displacement amount parameter can also be displayed in addition to the above.

The image processing unit 201 is capable of calculating the positioning parameter representing a displacement amount of the bed by the following formula using the deformation parameter and displacement amount parameter obtained in the above manner.

[Mathematical Formula 1]

$$x = \frac{\alpha_1 \vec{D}_1(x) + \alpha_2 \vec{D}_2(x) + \alpha_3 \vec{S}(x)}{\alpha_1 + \alpha_2 + \alpha_3}$$

$$y = \frac{\alpha_1 \vec{D}_1(y) + \alpha_2 \vec{D}_2(y) + \alpha_3 \vec{S}(y)}{\alpha_1 + \alpha_2 + \alpha_3}$$

$$z = \frac{\alpha_1 \vec{D}_1(z) + \alpha_2 \vec{D}_2(z) + \alpha_3 \vec{S}(z)}{\alpha_1 + \alpha_2 + \alpha_3}$$

$$rot\_x = \frac{\beta_1 \vec{D}_1(x) + \beta_2 \vec{D}_2(x) + \beta_3 \vec{S}(x)}{\beta_1 + \beta_2 + \beta_3}$$

$$rot\_y = \frac{\beta_1 \vec{D}_1(y) + \beta_2 \vec{D}_2(y) + \beta_3 \vec{S}(y)}{\beta_1 + \beta_2 + \beta_3}$$

$$rot\_z = \frac{\beta_1 \vec{D}_1(z) + \beta_2 \vec{D}_2(z) + \beta_3 \vec{S}(z)}{\beta_1 + \beta_2 + \beta_3}$$

Where D1 represents a (average) deformation amount obtained from a deformation parameter 1 for the whole image, D2 represents a (average) deformation amount obtained from a deformation parameter 2 for a target, and S represents a displacement amount obtained from the displacement amount parameter. Also, α1, α2, α3, β1, β2, and β3 are coefficients and can be defined as appropriate in advance. Letters x, y, z, rot_x, rot_y, and rot_z represent a displacement amount in an x direction, y direction, and z direction and rotation amount around an x axis, y axis, and z axis, respectively. The image processing unit 201 presents the displacement amount obtained in this manner on the display unit 203. The operator can move the bed using this as a reference.

The deformation amount and displacement amount of a target, OAR, displacement amount of the bed, respective regions, and the like for every treatment are accumulated in the deformation parameter DB, displacement amount parameter DB, extracted regions DB, and positioning parameter DB illustrated in FIG. 2. The image processing unit 201 can therefore easily display the information on the display unit 203 in the form of graph, table, or the like, which allows the operator to grasp the deformation amount and displacement amount of each part under treatment, displacement amount of the bed, and the like. Moreover, the image processing unit 201 can display a tendency (average, dispersion, etc.) of the deformation amount or displacement amount or changes over time using data accumulated from the past to the present on the display unit 203, thereby allowing for grasping such information.

In the aforementioned embodiments, the deformation parameter and displacement amount parameter are calculated from comparison between the treatment plan image and positioning image. However, calculating the deformation parameter, displacement amount parameter, and positioning parameter in a similar manner from a positioning image previously used and a positioning image imaged in the present treatment allows for obtaining a degree of deformation and displacement amount of a target or OAR, displacement amount of a bed, and the like during a therapy period.

Also in the aforementioned embodiments, the DICOM format is used for the formats (data format) of the treatment plan CT image and three-dimensional tomographic image. However, other formats can be surely used such as the JPEG image, bitmap image, or the like. Moreover, the image server 102 stores data files; however, the treatment planning device 101 and positioning system 104 may directly communicate to exchange the data files.

Furthermore, the embodiment where communication of data files or the like via a network is used has been described; however, other storage mediums such as a large-capacity storage medium including a flexible disc and CD-R may be used as a means for exchanging the data files. Also, a case where the irradiation object lies down on the bed 15 of the radiation therapy system 1 has been described; however, the present invention and present embodiment can be also applied to a case where bed positioning is performed with a bed similar to that of the radiation therapy system in a three-dimensional room. Radiation therapy where the present invention and present embodiments can be also applied to includes, not to mention X ray therapy devices, particle beam therapy devices using particle beams other than X rays.

4. Effects of Embodiments

According to the present embodiment, changes or displacement amount of the region of interest such as a target or organ at risk in radiation therapy are clarified for every treatment upon bed positioning in radiation therapy, especially upon positioning using a three-dimensional tomographic image, thereby allowing for bed positioning with a high accuracy.

In the present embodiment, especially, calculating the deformation parameter, displacement amount parameter, and positioning parameter obtained from the treatment plan image and positioning image visualizes a degree of deformation and displacement amount of a target or OAR, displacement amount of a bed, and the like. This enables evaluating the result of positioning, thereby allowing for positioning with a high accuracy. This allows the operator to easily confirm changes or displacement amount of a region of interest. Therefore, correction by the operator and time required for the correction can be reduced and time for positioning can be shortened. Thus, throughput of treatment can be enhanced.

Furthermore, the present embodiment allows for accumulation of the deformation parameter, displacement amount parameter, and positioning parameter, which are not calculated conventionally, for every treatment and viewing history of those parameters. Moreover, classifying the accumulated parameters by cases allows for grasping a tendency in deformation or displacement for each similar case, thereby enhancing accuracy of positioning.

5. Note

Incidentally, the present invention is not limited to the aforementioned examples but includes various variations. For example, the aforementioned examples are described in detail in order to facilitate understanding of the present invention and thus the present invention is not necessarily limited to include all of the configurations having been described. Apart of a configuration of one of the examples may be replaced with the configuration of another example. Also, a configuration of one of the examples may be added with a configuration of another example. Moreover, a part of a configuration of each of the examples may be added with, deleted of, or replaced with another configuration. A part or all of the aforementioned respective configurations, functions, processing units, processing means, or the like may be implemented by hardware by, for example designing with an integrated circuit. Also, the aforementioned respective configurations, functions, or the like may be implemented by software such that a processor interprets and executes a program implementing each of the functions. Information such as a program, table, or file implementing the respective functions may be placed in a storage device such as a memory, hard disc, or solid state drive (SSD) or a storage medium such as an IC card, SD card, or DVD. Incidentally, only control lines or data lines that are considered necessary for the purpose of description are illustrated and thus all of control lines or data lines in a product are not always illustrated. In fact, it can be assumed that substantially all of the configurations are connected with each other.

REFERENCE SIGNS LIST 1 radiation therapy system
10 radiation irradiation system
11 control unit
12 radiation generator
13 transport system
14 irradiation device
15 bed
101 treatment planning device
102 image server
103 three-dimensional tomographic imaging device
104 positioning system
105 bed-driving device
201 image processing unit
202 input unit
203 display unit
204 deformation parameter database
205 displacement amount parameter database
206 extracted region database
207 image alignment unit
208 region extraction unit
209 region deformation unit
210 deformation parameter calculation unit
211 displacement amount parameter calculation unit
212 deformation parameter evaluation unit
213 displacement amount parameter evaluation unit
1001 positioning result display screen

The invention claimed is:

1. A radiation therapy apparatus, comprising:
an image processing unit; and
a display unit,
wherein the image processing unit is configured to:
receive a treatment plan image imaged in advance as a tomographic image and information of a region of interest including a target and/or an organ at risk generated by a treatment planning device and receive a positioning image imaged by a tomographic imaging device for positioning the target for irradiation of radioactive rays;
perform alignment of the treatment plan image and the positioning image;
calculate a first deformation parameter representing deformation between the aligned treatment plan image and the positioning image based on a degree of deformation of the entire positioning image relative to the aligned treatment plan image;

extract a first region in the region of interest in the aligned treatment plan image and a second region in the region of interest in the positioning image;

calculate a second deformation parameter representing deformation between the aligned treatment plan image and the positioning image based on a degree of deformation of the first region and the second region;

calculate a third deformation parameter based on a degree of deformation of the entire positioning image relative to the aligned treatment plan image, or use the first deformation parameter as the third deformation parameter;

apply the third deformation parameter to the region of interest in the treatment plan image and calculate a deformed region of interest;

calculate a first characteristic region which is common to a region corresponding to the region of interest in the treatment plan image and a characteristic region in the region of interest in the treatment plan image, calculate a second characteristic region which is common to a region corresponding to the deformed region of interest in the positioning image and a characteristic region in the region of interest in the positioning image;

calculate a displacement amount parameter representing displacement from the region of interest in the treatment plan image to the region of interest in the positioning image with regard to the first characteristic region and the second characteristic region;

calculate a plurality of positioning parameters representing a position displacement amount and rotation amount of a bed based on the first and second deformation parameters and the displacement amount parameter;

display one or more of an image representing the first deformation parameter, an image representing the second deformation parameter, an image representing the displacement amount parameter, and an image representing the positioning parameters on the display unit; and output the positioning parameters to cause the bed to move and rotate.

2. The radiation therapy apparatus according to claim 1, wherein a moving vector of each of centroids of the first characteristic region and second characteristic region is the displacement amount parameter or a moving vector obtained from comparison of contour outlines is the displacement amount parameter.

3. The radiation therapy apparatus according to claim 1, wherein the image processing unit calculates each of the first and second characteristic regions as a common region by means of a logical add or a logical multiply.

4. The radiation therapy apparatus according to claim 1, wherein the image processing unit is further configured to:

calculate the positioning parameters representing a position displacement amount and rotation amount of the bed in six degrees of freedom using a deformation amount obtained from the first deformation parameter, a deformation amount obtained from the second deformation parameter, and a displacement amount obtained from the displacement amount parameter based on predetermined weighting and an expression.

5. The radiation therapy apparatus according to claim 1, wherein the image processing unit includes:

a deformation parameter database configured to store the first deformation parameter and the second deformation parameter;

a displacement amount parameter database configured to store the displacement amount parameter; and a positioning parameter database configured to store the positioning parameters.

6. The radiation therapy system according to claim 1, further comprising:

a treatment planning device configured to generate the treatment plan image which is imaged in advance as a tomographic image and information of the region of interest including the target and/or the organ at risk in order to produce the treatment plan of radiation therapy;

a tomographic imaging device configured to generate, as a tomographic image, the positioning image for positioning of the target of irradiation of radioactive rays; and a positioning system configured to execute a bed positioning processing which positions the bed based on the output positioning parameters.

7. The radiation therapy system according to claim 6, further comprising:

an image server configured to store the treatment plan image and information of the region of interest and/or the positioning image and to be accessed by the positioning system.

8. The radiation therapy system according to claim 7, wherein the tomographic imaging device images and stores, in the image server, the treatment plan image, and the treatment planning device reads the treatment plan image for planning the treatment plan from the image server, sets the region of interest including the target and organ at risk, and stores the information of the region of interest in the image server together with the treatment plan image.

9. The radiation therapy system according to claim 6, further comprising:

a bed-driving device configured to input thereto the positioning parameters from the positioning system and to move and rotate the bed based on the positioning parameters.

10. A radiation therapy apparatus, comprising:

an image processing unit;

a storage device; and a display unit, wherein the image processing unit is configured to:

receive a treatment plan image imaged in advance as a tomographic image and information of a region of interest including a target and/or an organ at risk generated by a treatment planning device and receive a positioning image imaged by a tomographic imaging device for positioning the target for irradiation of radioactive rays;

perform alignment of the treatment plan image and the positioning image;

calculate a first deformation parameter and a second deformation parameter representing deformation in a whole image and deformation in a partial image, respectively, between the aligned treatment plan image and the positioning image;

calculate a displacement amount parameter representing displacement from the region of interest in the treatment plan image to the region of interest in the positioning image;

calculate a plurality of positioning parameters representing a position displacement amount and rotation amount of a bed based on the first and second deformation parameters and the displacement amount parameter;

display one or more of an image representing the first deformation parameter, an image representing the second deformation parameter, an image representing the displacement amount parameter, and an image representing the positioning parameters on the display unit; and output the positioning parameters to cause the bed to move and rotate, wherein the storage device is configured to store:

a deformation parameter database configured to store the first deformation parameter and the second deformation parameter;

a displacement amount parameter database configured to store the displacement amount parameter; and a positioning parameter database configured to store the positioning parameters, and wherein the image processing unit is further configured to:

obtain and display, on the display unit, an average, a dispersion, or changes over time of one or more of a deformation amount of the region of interest, a displacement amount of the region of interest, position displacement amount and rotation amount of the bed using data accumulated in one or more of the deformation parameter database, displacement amount parameter database, and the positioning parameter database.

11. The radiation therapy apparatus according to claim 1, wherein the image processing unit is further configured to:

display, on the display unit, one or more of the treatment plan image, positioning image, and a fusion image where both of the images overlap and thereby displayed.

12. The radiation therapy system according to claim 10, further comprising:

a treatment planning device configured to generate the treatment plan image which is imaged in advance as a tomographic image and information of the region of interest including the target and/or the organ at risk in order to produce the treatment plan of radiation therapy;

a tomographic imaging device configured to generate, as a tomographic image, the positioning image for positioning of the target of irradiation of radioactive rays; and a positioning system configured to execute a bed positioning processing which positions the bed based on the output positioning parameters.

13. The radiation therapy system according to claim 12, further comprising:

a bed-driving device configured to input thereto the positioning parameters from the positioning system and to move and rotate the bed based on the positioning parameters.

14. A radiation therapy apparatus, comprising:

an image processing unit; and a display unit, wherein the image processing unit is configured to:

receive a treatment plan image imaged in advance as a tomographic image and information of a region of interest including a target and/or an organ at risk generated by a treatment planning device and receive a positioning image imaged by a tomographic imaging device for positioning the target for irradiation of radioactive rays;

perform alignment of the treatment plan image and the positioning image;

calculate a first deformation parameter and a second deformation parameter representing deformation in a whole image and deformation in a partial image, respectively, between the aligned treatment plan image and the positioning image;

calculate a displacement amount parameter representing displacement from the region of interest in the treatment plan image to the region of interest in the positioning image;

calculate a plurality of positioning parameters representing a position displacement amount and rotation amount of a bed based on the first and second deformation parameters and the displacement amount parameter;

display one or more of an image representing the first deformation parameter, an image representing the second deformation parameter, an image representing the displacement amount parameter, and an image representing the positioning parameters, and display one or more of the treatment plan image, positioning image, and a fusion image where both of the images overlap on the display unit; and output the positioning parameters to cause the bed to move and rotate, wherein the image processing unit displays, on the display unit, one or more of the treatment plan image, positioning image, and a fusion image where both of the images overlap and thereby displayed, wherein the image processing unit includes:

an image alignment unit configured to align the treatment plan image and the positioning image;

a region extraction unit configured to extract the region of interest from the treatment plan image and the positioning image;

a region deformation unit configured to deform a region based on the alignment result obtained from the image alignment unit;

a deformation parameter calculation unit configured to calculate the first and second deformation parameters; and a displacement amount parameter calculation unit configured to calculate the displacement amount parameter based on the treatment plan image and the positioning image.

15. The radiation therapy system according to claim 14, further comprising:

a treatment planning device configured to generate the treatment plan image which is imaged in advance as a tomographic image and information of the region of interest including the target and/or the organ at risk in order to produce the treatment plan of radiation therapy;

a tomographic imaging device configured to generate, as a tomographic image, the positioning image for positioning of the target of irradiation of radioactive rays; and a positioning system configured to execute a bed positioning processing which positions the bed based on the output positioning parameters.

16. The radiation therapy system according to claim 15, further comprising:

a bed-driving device configured to input thereto the positioning parameters from the positioning system and to move and rotate the bed based on the positioning parameters.

* * * * *